(12) United States Patent
Sato et al.

(10) Patent No.: US 8,278,625 B2
(45) Date of Patent: Oct. 2, 2012

(54) TWO-DIMENSIONAL POSITION MAP CORRECTING METHOD

(75) Inventors: Masanobu Sato, Kizugawa (JP); Yoshihiro Yamada, Kyoto (JP); Nobuya Hashizume, Kyoto (JP); Keishi Kitamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 217 days.

(21) Appl. No.: 12/919,431

(22) PCT Filed: Mar. 21, 2008

(86) PCT No.: PCT/JP2008/055306
§ 371 (c)(1),
(2), (4) Date: Aug. 25, 2010

(87) PCT Pub. No.: WO2009/116174
PCT Pub. Date: Sep. 24, 2009

(65) Prior Publication Data
US 2011/0001050 A1 Jan. 6, 2011

(51) Int. Cl.
*G01T 1/10* (2006.01)
(52) U.S. Cl. .................................. 250/362
(58) Field of Classification Search .......... 250/362, 250/363.01–363.1
See application file for complete search history.

(56) References Cited

FOREIGN PATENT DOCUMENTS
JP 2005-43104 A 2/2005

OTHER PUBLICATIONS

Hu et al., "A neural network based algorithm for building crystal look-up table of PET block detector," 2006, IEEE Nuclear Science Symposium Conference Record, vol. M11-79, pp. 2458-2461.*
Lee et al., "Detector characteristics of the micro crystal element scanner (MiCES)," 2005, IEEE Transactions on Nuclear Science, vol. 52, No. 5, pp. 1428-1433.*
International Search Report for the Application No. PCT/JP2008/055306 mailed Jun. 3, 2008.
Modegi, Toshio et al., "Development of Integrated Calibration Assistant Tool for Pixel-PSPMT Type Gamma Camera", IEICE Technical Report, 2006, vol. 106, No. 75, pp. 55-60.

* cited by examiner

*Primary Examiner* — Kiho Kim
(74) *Attorney, Agent, or Firm* — Cheng Law Group, PLLC (57) ABSTRACT

A radiation detecting apparatus of this invention includes an arithmetic processing device which has a first adding step for adding signal strengths in one portion of a two-dimensional position map, draws respective boundaries based on results of addition in the first adding step, and corrects the two-dimensional position map based on signal strengths enclosed by these boundaries. The signal strengths of one portion of the two-dimensional position map, and not all the areas of the two-dimensional position map, are added. As a result, incident positions can be discriminated efficiently, and radiation detecting positions can be determined efficiently.

5 Claims, 7 Drawing Sheets

○ : 1st Layer
◇ : 2nd Layer
⬡ : 3rd Layer
☐ : 4th Layer

TWO-DIMENSIONAL POSITION MAP CORRECTING METHOD

TECHNICAL FIELD

This invention relates to a two-dimensional position map correcting method for correcting a two-dimensional position map used when detecting radiation with radiation detectors each including a plurality of scintillator elements and a light sensor optically connected thereto.

BACKGROUND ART

A PET (Positron Emission Tomography) apparatus will be described as an example of nuclear medicine diagnostic apparatus, i.e. ECT (Emission Computed Tomography) apparatus. The PET apparatus is constructed to detect a plurality of γ-rays generated by annihilation of positrons, and to reconstruct a sectional image of a patient only when a plurality of detectors simultaneously detect the γ-rays.

Specifically, a patient is medicated with a radioactive drug including a positron-emitting radionuclide, and detectors consisting of numerous detecting element (e.g. scintillator) groups detect pair annihilation γ-rays of 511 KeV released from the patient medicated. And when two detectors detect γ-rays within a definite period of time, they are counted as one pair of annihilation γ-rays detected as a coincidence, and a pair annihilation generating point is determined to exist on a straight line linking the detector pair having detected them. Such coincidence information is accumulated and reconstruction is carried out to obtain a positron-emitting radionuclide distribution image (i.e. a sectional image).

At this time, image resolution of the sectional image is improved by discriminating not only γ-ray detecting positions (γ-ray incident positions) on the detectors but γ-ray detecting positions on the scintillators as more particular γ-ray detecting positions, to increase γ-ray detecting accuracy. So, the number of scintillators is increased to increase discriminating capability. In recent years, in particular, DOI detectors have been developed, which have scintillators laminated also in a depth direction to be capable of discriminating light source positions having caused interaction in the depth direction (DOI: Depth of Interaction).

Figure 10:
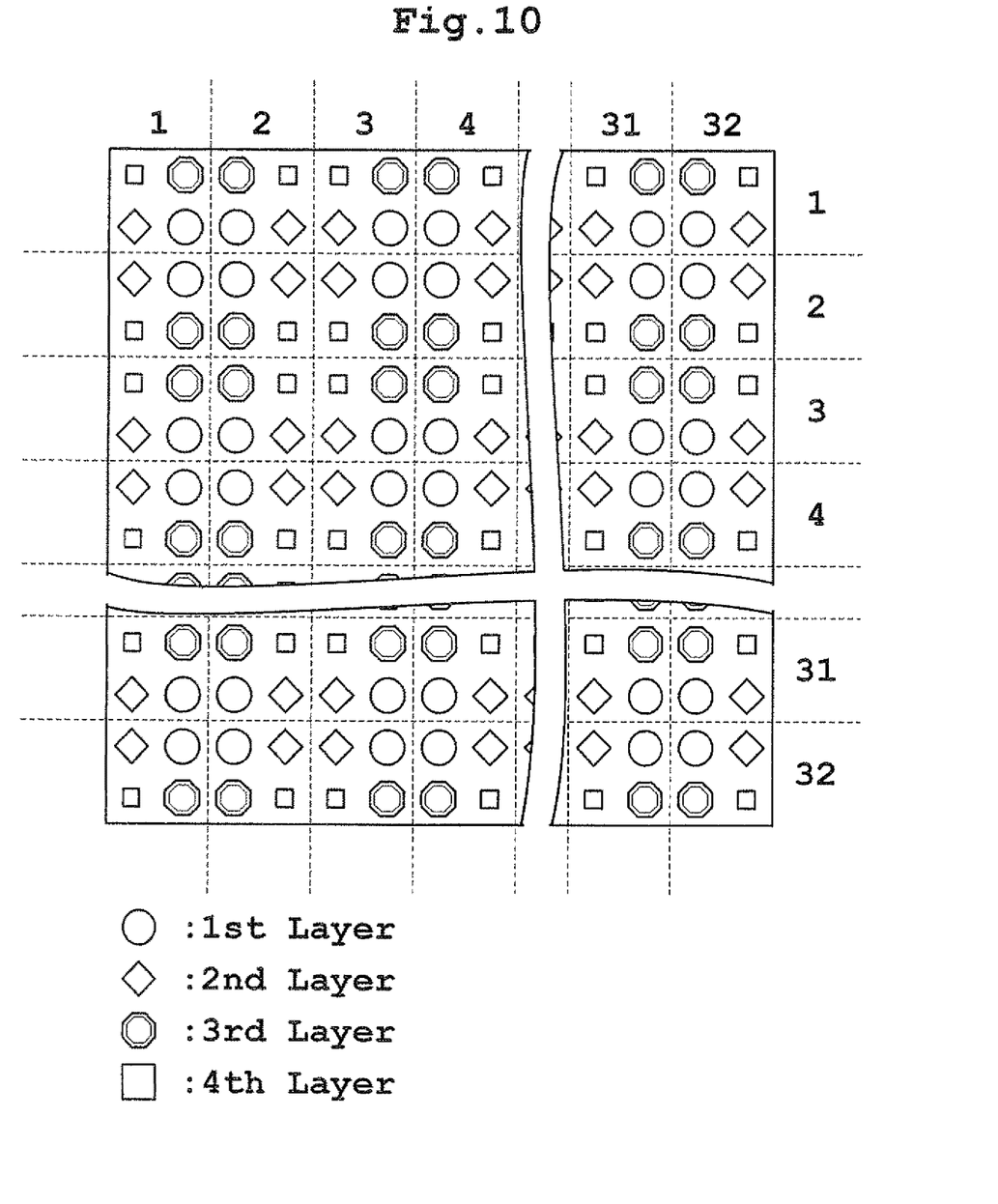
FIG. 10 is a plan view of a two-dimensional position map in the case of a DOI detector having four layers of scintillators laminated in a depth direction.

To discriminate γ-ray incident positions, a two-dimensional position map prepared beforehand is used. The two-dimensional position map is a map showing, in two dimensions, the number of luminescent photons (corresponding to a count value of γ-rays) obtained with light sensors represented by photomultiplier tubes (PMT), as corresponding to incident positions of γ-ray incident on the scintillators. FIG. 10 shows a two-dimensional position map in the case of a DOI detector having four layers of scintillators laminated in the depth direction. The positions indicated by white circles (shown as "○" in FIG. 10) are scintillators in the first layer (written "1st Layer" in FIG. 10). The positions indicated by white rhombuses are scintillators in the second layer (written "2nd Layer" in FIG. 10). The positions indicated by white double octagons are scintillators in the third layer (written "3rd Layer" in FIG. 10). The positions indicated by white rectangles (shown as "□" in FIG. 10) are scintillators in the fourth layer (written "4th Layer" in FIG. 10). Incident positions of actually incident γ-rays can be discriminated by referring to a look-up table (LUT) having each position in the two-dimensional position map corresponding to each scintillator, and referring to the two-dimensional position map.

Incidentally, where a plurality of scintillators are arranged in three dimensions as in the DOI detector, diffusion is provided by combination of a light reflective material and a light transmissive material, for example, between adjoining scintillators, so that positions do not overlap in the two-dimensional position map. Further, a technique of correcting the two-dimensional position map has been introduced, which carries out a statistical clustering process in order to increase the discriminating capability still further (see Patent Document 1, for example).

[Patent Document 1]
Unexamined Patent Publication No. 2005-43104

DISCLOSURE OF THE INVENTION

Problem to be Solved by the Invention

However, the scintillator elements of the DOI detector become numerous, and the number of areas corresponding to the scintillator elements increases on the two-dimensional position map. Therefore, in Patent Document 1 noted above, a presumption in the statistical clustering process will take time. When peak detection is carried out on the two-dimensional position map for area division, the accuracy of detecting a peak position worsens due to the problem of statistical accuracy of the two-dimensional position map. When division is carried out by adding count values of the entire two-dimensional position map, to partition it into a grid form, and the two-dimensional position map has distortion, the areas cannot be divided accurately. Further, since the number of areas on the two-dimensional position map is huge, when the areas are manually divided, the operation will consume a very long time.

This invention has been made having regard to the state of the art noted above, and its object is to provide a two-dimensional position map correcting method which can correct a two-dimensional position map accurately and efficiently even when there is distortion.

Means for Solving the Problem

To fulfill the above object, this invention provides the following construction.

A two-dimensional position map correcting method of this invention is a two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising a first adding step for adding the signal strengths in one portion of the two-dimensional position map, wherein respective boundaries are drawn based on results of addition in the first adding step, and the two-dimensional position map is corrected based on signal strengths enclosed by these boundaries, and wherein the first adding step is executed to add the signal strengths of each portion of the two-dimensional position map, and the above method comprises a boundary drawing step for drawing the respective boundaries by comparing results of addition of each portion in the first adding step; a second adding step for adding the signal strengths at the respective boundaries; an area setting step for setting one reference area based on results of addition in the second adding step; a delimiting reference point determining step for determining respective delimiting reference points based on respective signal strengths in the reference area set in the area setting step; and a boundary redrawing step for redrawing respective boundaries along the respective delimiting reference points determined in the delimiting reference point determining step; the two-dimensional position map being corrected based on signal strengths enclosed by the boundaries redrawn in the boundary redrawing step.

According to the two-dimensional position map correcting method of this invention, a first adding step is provided for adding the signal strengths in one portion of the two-dimensional position map. After drawing respective boundaries based on results of addition in the first adding step, the two-dimensional position map is corrected based on signal strengths enclosed by these boundaries. Since the signal strengths of one portion of the two-dimensional position map, and not all the areas of the two-dimensional position map, are added, the two-dimensional position map can be corrected efficiently.

In the above boundary drawing step, the respective boundaries are drawn by comparing results of addition of the each portion in the first adding step, but they are not boundaries taking distortion into consideration, and the areas enclosed by the boundaries are not exact, either. Then, the second adding step is executed to add signal strengths at the respective boundaries, and the area setting step is executed to set one reference area based the results of addition in the second adding step. And the delimiting reference point determining step is executed to determine respective delimiting reference points based on the respective signal strengths in the reference area set in the area setting step. In the subsequent boundary redrawing step, the respective boundaries are redrawn along the respective delimiting reference points determined in the delimiting reference point determining step.

When the above boundary drawing step, second adding step, area setting step, delimiting reference point determining step and boundary redrawing step are provided, it is preferable to provide the following altering step. That is to provide an altering step for altering positions of delimiting points to be altered, by comparing respective signal strengths around the delimiting points to be altered, while successively and contiguously moving from one to another of the boundaries redrawn in the boundary redrawing step, with reference to the area set in the area setting step. The respective boundaries are redrawn based on results of addition in the altering step. With this boundary redrawing, the boundaries have distortion taken into consideration, and the areas enclosed by the boundaries are also accurate. Thus, the two-dimensional position map can be corrected accurately even when there is distortion.

The farther away from the area set in the area setting step, the larger becomes distortion. Therefore, in the altering step, the positions of delimiting points to be altered are altered by comparing respective signal strengths around the delimiting points to be altered, while successively and contiguously moving from one to another of the boundaries redrawn in the boundary redrawing step. Thus, the positions of delimiting points are altered while successively and contiguously moving from one to another of the boundaries redrawn in the boundary redrawing step, with reference to the area set in the area setting step. The positions of delimiting points can be altered accurately using respective surrounding signal strengths already altered. Therefore, each boundary is redrawn based on an alteration result in the altering step, and the areas enclosed by these boundaries have increased accuracy, allowing the two-dimensional position map to be corrected with increased accuracy.

When the above altering step is provided, it is further preferable to provide the following re-altering step. That is, it is further preferable to provide an re-altering step for re-altering the positions of the delimiting points by comparing respective delimiting points belonging to the boundaries redrawn based on results of alteration in the altering step, wherein the respective boundaries are redrawn based on results of re-alteration in the re-altering step, and the two-dimensional position map is corrected based on signal strengths enclosed by these boundaries.

In the re-altering step, the positions of delimiting points are re-altered by comparing the respective delimiting points belonging to the boundaries redrawn based on the alteration results in the altering step. That is, discontinuity will remain even if each boundary is redrawn based on the alteration results in the preceding altering step. Then, whether discontinuity or continuity is determined by comparing the respective delimiting points belonging to the boundaries redrawn based on the alteration results in the altering step, and in the discontinuous case, the positions of delimiting points are re-altered. Since the positions of delimiting points are re-altered in this way by comparing the respective delimiting points belonging to the boundaries redrawn based on the alteration results in the altering step, discontinuity can be eliminated and the delimiting points can be re-altered with increased accuracy. Therefore, each boundary is redrawn based on the results of re-alteration in the re-altering step, and the areas enclosed by these boundaries will also become further accurate to allow the two-dimensional position map to be corrected with increased accuracy.

In these inventions providing the above boundary drawing step, second adding step, area setting step, delimiting reference point determining step and boundary redrawing step, it is preferred that the boundary drawing step is executed to obtain respective local minimal values by comparing the results of addition of each portion in the first adding step, and to draw the respective boundaries along positions of these local minimal values. The respective boundaries can be drawn accurately by obtaining the local minimal values.

Similarly, it is preferred that the delimiting reference point determining step is executed to obtain respective local minimal values by comparing the signal strengths in the reference area set in the area setting step, and to determine positions of these local minimal values to be the delimiting reference points. The delimiting reference points can be determined accurately by obtaining the local minimal values.

Effects of the Invention

With the two-dimensional position map correcting method according to this invention, a first adding step is provided for adding the signal strengths in one portion of a two-dimensional position map. After drawing respective boundaries based on results of addition in the first adding step, a two-dimensional position map is corrected based on signal strengths enclosed by these boundaries. Since the signal strengths of one portion of the two-dimensional position map, and not all the areas of the two-dimensional position map, are added, the two-dimensional position map can be corrected efficiently.

Further, a second adding step is executed to add signal strengths at the respective boundaries, and an area setting step is executed to set one reference area based the results of addition in the second adding step. A delimiting reference point determining step is executed to determine respective delimiting reference points based on the respective signal strengths in the reference area set in the area setting step. And, in a subsequent boundary redrawing step, the respective boundaries are redrawn along the respective delimiting reference points determined in the delimiting reference point determining step. With this boundary redrawing, the boundaries have distortion taken into consideration, and the areas enclosed by the boundaries are also accurate. Thus, the two-dimensional position map can be corrected accurately even when there is distortion.

BRIEF DESCRIPTION OF THE DRAWINGS

FIG. 3(a) is a plan view of the γ-ray detector, and (b) is a side view of the γ-ray detector;

DESCRIPTION OF REFERENCES

3 . . . γ-ray detectors
10 . . . look-up table
13 . . . two-dimensional position map correcting unit
31 . . . scintillator block
32 . . . photomultiplier tube (PMT)
M . . . two-dimensional position map

[Embodiment]

Figure 1:
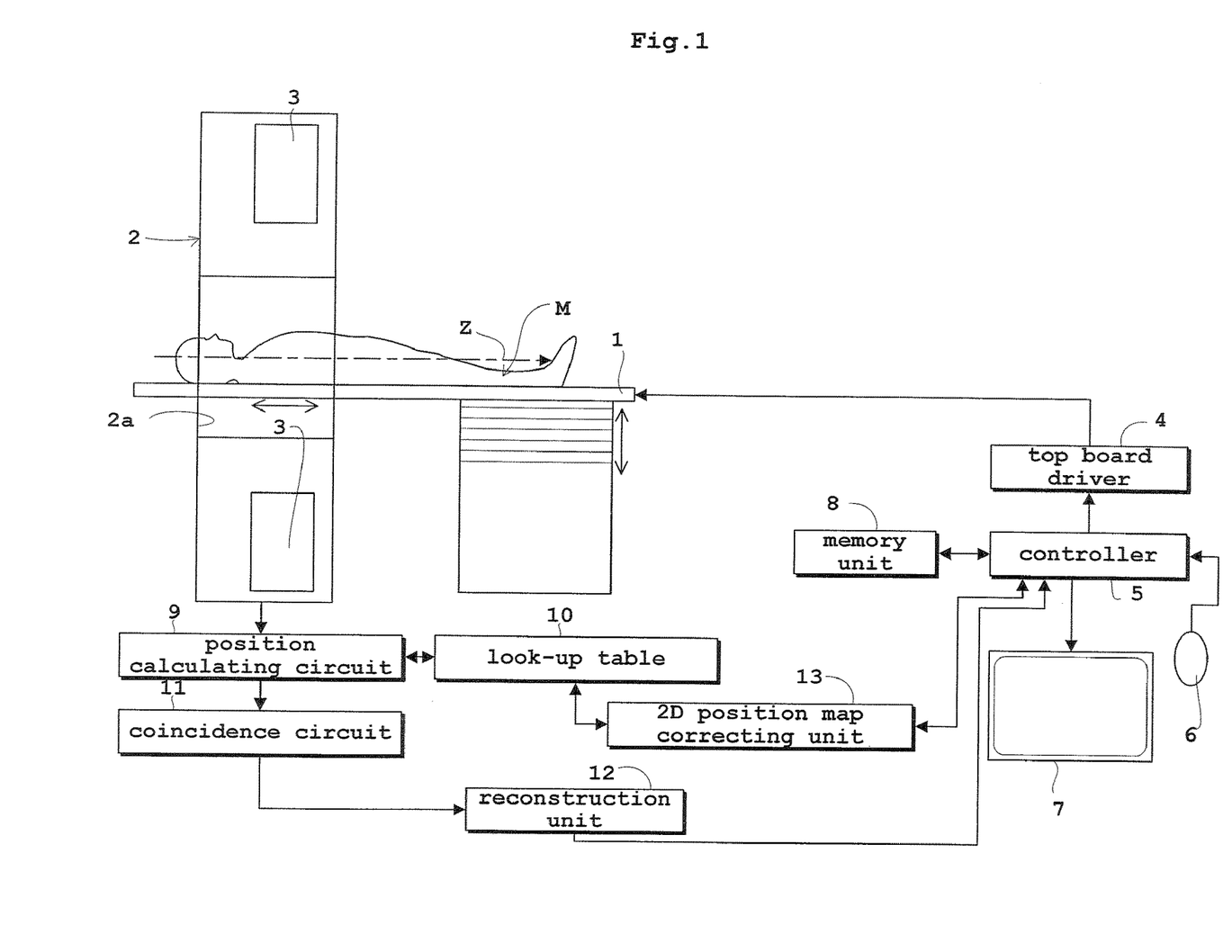
FIG. 1 is a side view and block diagram of a PET (Positron Emission Tomography) apparatus according to an embodiment.
Figure 2:
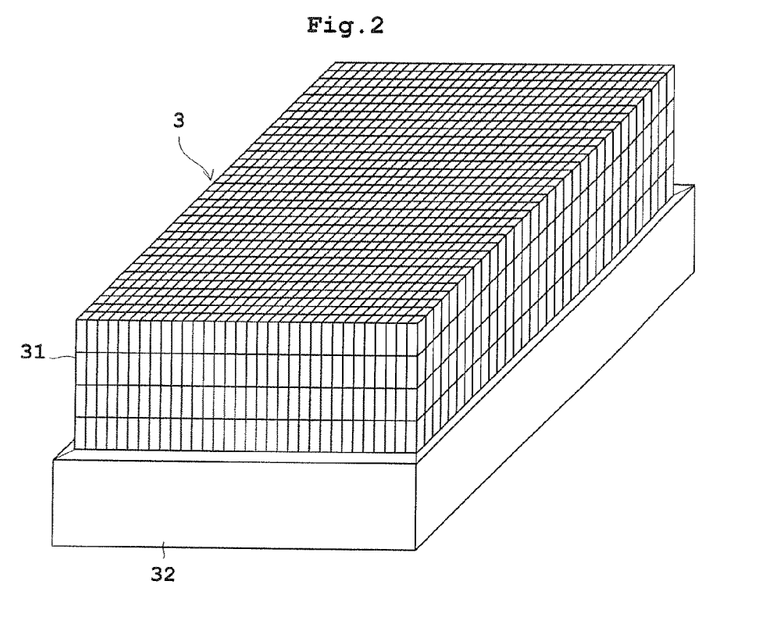
FIG. 2 is a schematic perspective view of a γ-ray detector.
Figure 3:
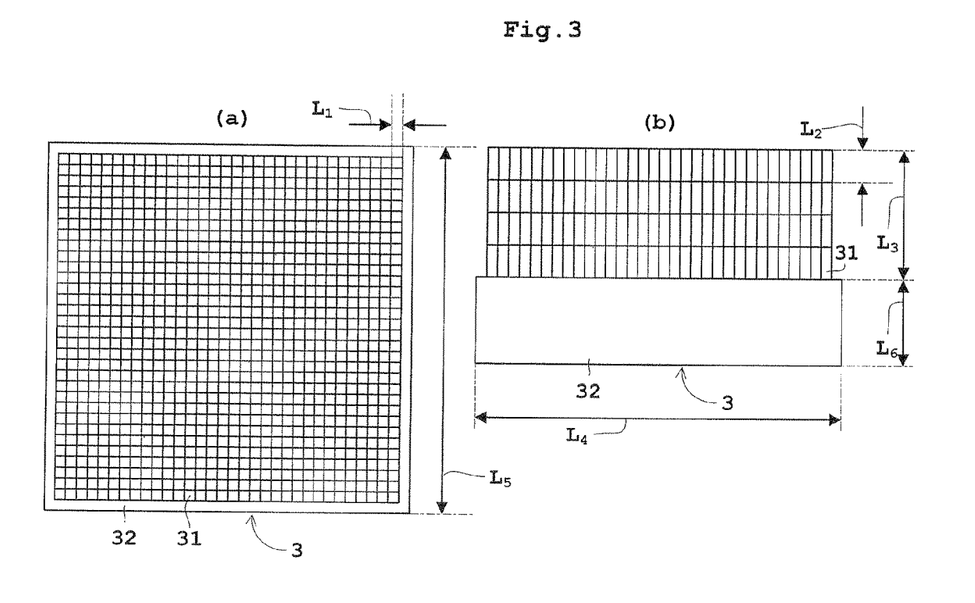

An embodiment of this invention will be described hereinafter with reference to the drawings. FIG. 1 is a side view and block diagram of a PET (Positron Emission Tomography) apparatus according to the embodiment. FIG. 2 is a schematic perspective view of a γ-ray detector. FIG. 3 (a) is a plan view of the γ-ray detector. FIG. 3(b) is a side view of the γ-ray detector.

The PET apparatus according to this embodiment, as shown in FIG. 1, includes a top board 1 for supporting a patient M. This top board 1 is constructed to move up and down and make parallel translation along the body axis Z of the patient M. With this construction, the patient M placed on the top board 1 passes through an opening 2a of a gantry 2 described hereinafter, to be scanned in order from the head to the abdomen and the feet, to obtain images of the patient M. There is no limitation as to the sites scanned or the scanning sequence of the respective sites.

The PET apparatus according to this embodiment includes the gantry 2 with the opening 2a and γ-ray detectors 3, besides the top board 1. The γ-ray detectors 3 are arranged in a ring form so as to surround the body axis Z of the patient M, and are embedded in the gantry 2. The γ-ray detectors 3 correspond to the radiation detectors in this invention.

In addition, the PET apparatus according to this embodiment includes a top board driver 4, a controller 5, an input unit 6, an output unit 7, a memory unit 8, a position calculating circuit 9, a look-up table 10, a coincidence circuit 11, a reconstruction unit 12 and a two-dimensional position map correcting unit 13. The top board driver 6 is a mechanism for driving the top board 1 to make the above movements, and has a motor not shown. The look-up table 10 corresponds to the storage device in this invention. The two-dimensional position map correcting unit 13 corresponds to the arithmetic processing device in this invention. The gantry 2, γ-ray detectors 3, position calculating circuit 9, look-up table 10, coincidence circuit 11 and two-dimensional position map correcting unit 13 constitute the radiation detecting apparatus in this invention.

The controller 5 performs overall control of the components forming the PET apparatus according to this embodiment. The controller 5 includes a central processing unit (CPU) and others.

The input unit 6 feeds the controller 5 with data and commands inputted by the operator. The input unit 6 includes a pointing device represented by a mouse, keyboard, joystick, trackball and/or touch panel. The output unit 7 includes a display unit represented by a monitor, a printer, and so on.

The memory unit 8 and look-up table 10 are formed of storage media represented by a ROM (Read-only Memory), RAM (Random-Access Memory) and the like. In this embodiment, a count of coincidences counted by the coincidence circuit 11 and images processed by the reconstruction unit 12 are written and stored in a RAM, and are read from the RAM as necessary. In this embodiment, in particular, a two-dimensional position map showing, in two dimensions, counts corresponding to signal strengths of electric signals acquired from photomultiplier tubes 33 (see FIGS. 2 and 3) described hereinafter, and made to correspond to incident positions of γ-rays incident on scintillator elements of scintillator blocks 31 (see FIGS. 2 and 3) described hereinafter, is written and stored in the look-up table 10 as a table having each position in the two-dimensional position map and each scintillator element in a corresponding relationship, which is read from the look-up table 10 at a time of correction of the two-dimensional position map by the two-dimensional position map correcting unit 13, and detection signals of γ-rays are made to correspond to crystal elements with reference to the table. Programs for carrying out various types of nuclear medicine diagnosis and arithmetic processes relating to the flows in FIGS. 4 and 5 described hereinafter are stored beforehand in a ROM. With the controller 5 executing the programs, the nuclear medicine diagnosis and arithmetic processes relating to the flows in FIGS. 4 and 5 according to the programs are carried out.

The reconstruction unit 12 and two-dimensional position map correcting unit 13 are realized by the controller 5 executing, for example, a program stored in the ROM of the storage medium represented by the above memory unit 8, or the commands inputted with a pointing device represented by the input unit 6.

The scintillator blocks 31 (see FIGS. 2 and 3) of the γ-ray detectors 3 convert into light the γ-rays generating from the patient M medicated with a radioactive drug. The photomultiplier tubes (PMT) 32 (see FIGS. 2 and 3) of the γ-ray detectors 3 multiply the converted light and convert it into electric signals. The electric signals are fed to the position calculating circuit 9 as image information (pixel values, i.e. a count of coincidences counted by the γ-ray detectors 3).

The position calculating circuit 9 refers to the look-up table 10 and refers to the two-dimensional position map at a time of nuclear medicine diagnosis, and determines which scintillator elements of the scintillator blocks 31 (see FIGS. 2 and 3)

the count has occurred from. Specifically, incident positions on the scintillator elements are determined from a centroid calculation carried out at every incidence. The incident positions and counts (image information) obtained are fed to the coincidence circuit 11.

Specifically, when the patient M is medicated with a radioactive drug, two γ-rays are generated by annihilation of positrons of positron emission type RI. The coincidence circuit 11 checks positions of the scintillator blocks 31 (see FIGS. 2 and 3) (more particularly, positions of incidence on the scintillator elements) and incidence timing of the γ-rays, and determines received image information to be proper data only when the γ-rays are incident on two scintillator blocks 31 at opposite sides of the patient M at the same time. The coincidence circuit 11 ignores γ-rays incident only on one scintillator block 31.

Image information fed to the coincidence circuit 11 is fed as projection data to the reconstruction unit 12. The reconstruction unit 12 reconstructs the projection data to obtain images of the patient M. The images are fed to the output unit 7 through the controller 5. In this way, nuclear medicine diagnosis is carried out based on the images obtained by the reconstruction unit 12.

A γ-ray detector 3, as shown in FIGS. 2 and 3, includes a scintillator block 31 formed of a plurality of scintillator elements, and a photomultiplier tube (hereinafter abbreviated simply as "PMT") 32 optically coupled to the scintillator block 31. Each scintillator element forming the scintillator block 31 emits light with incidence of a γ-ray, thereby converting the γ-ray into light. The scintillator element detects the γ-ray by this conversion. The light emitted from the scintillator elements is fully diffused in the scintillator block 31, and is inputted to the PMT 32. The PMT 32 multiplies the light converted by the scintillator block 31, and converts it into electric signals. The electric signals are fed as image information (pixel values) to the position calculating circuit 9 (see FIG. 1) and also to the coincidence circuit 11 (see FIG. 1) as described above. The scintillator elements forming the scintillator block 31 correspond to the scintillator elements in this invention. The photomultiplier tube (PMT) 32 corresponds to the light sensor in this invention.

As shown in FIG. 3, one side of a scintillator element is set to $L_1$, the height of a scintillator element to $L_2$, the height of the scintillator block 31 to $L_3$, the width in the transverse direction of PMT 32 to $L_4$, the width in the longitudinal direction of PMT 32 to $L_5$, and the height of PMT 32 to $L_6$. This embodiment uses γ-ray detectors 3 of $L_1$=1.45 mm, $L_2$=4.5 mm, $L_3$=18 mm, $L_4$=52 mm, $L_5$=49.5 mm, and $L_6$=12.4 mm. Of course, each size of the γ-ray detectors 3 is not limited to this. This embodiment uses γ-ray detectors 3 with the scintillator block 31 having scintillator elements arranged in 32×32×4 layers, and the PMT 32 with 16×16 multi-anodes. There is no limitation as to the number of scintillator elements forming the scintillator block 31 or the number of multi-anodes of PMT 32.

Figure 4:
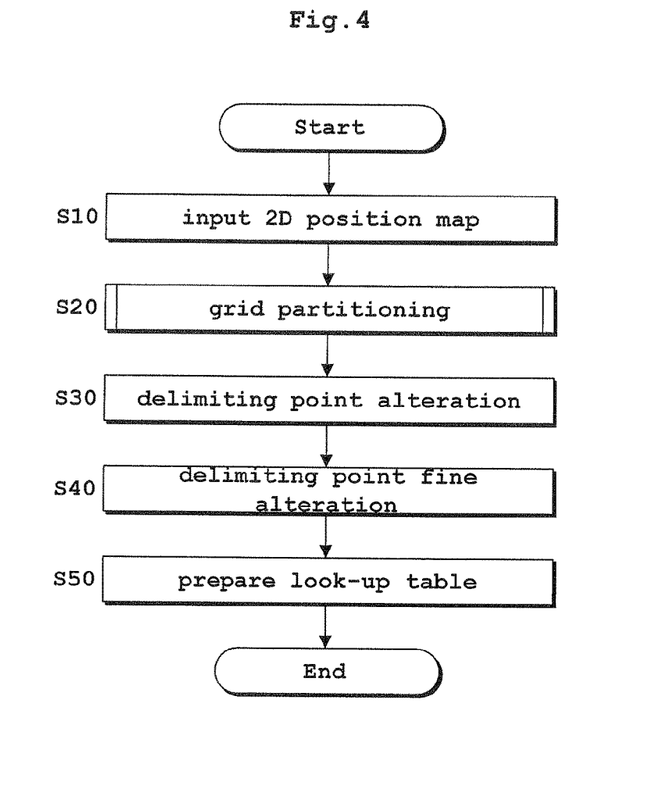
FIG. 4 is a flow chart showing arithmetic processes by a two-dimensional position map correcting unit.
Figure 5:
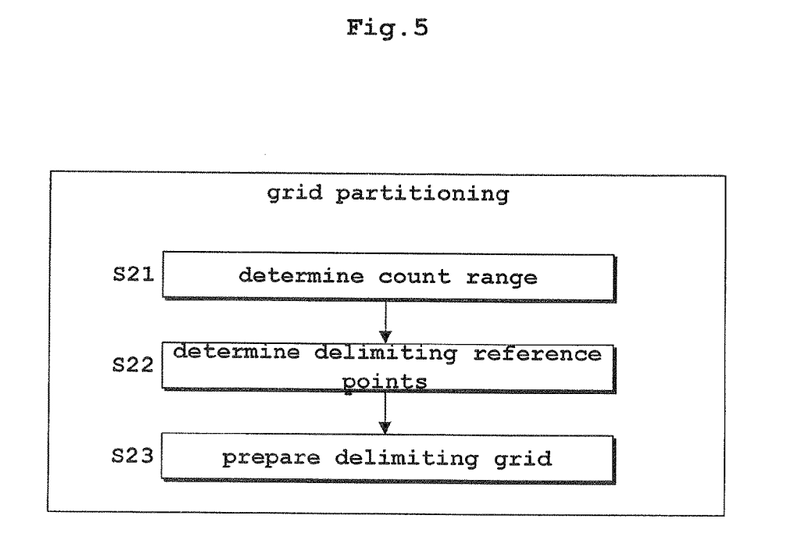
FIG. 5 is a flow chart showing arithmetic processes of grid partitioning in FIG. 4.
Figure 6:
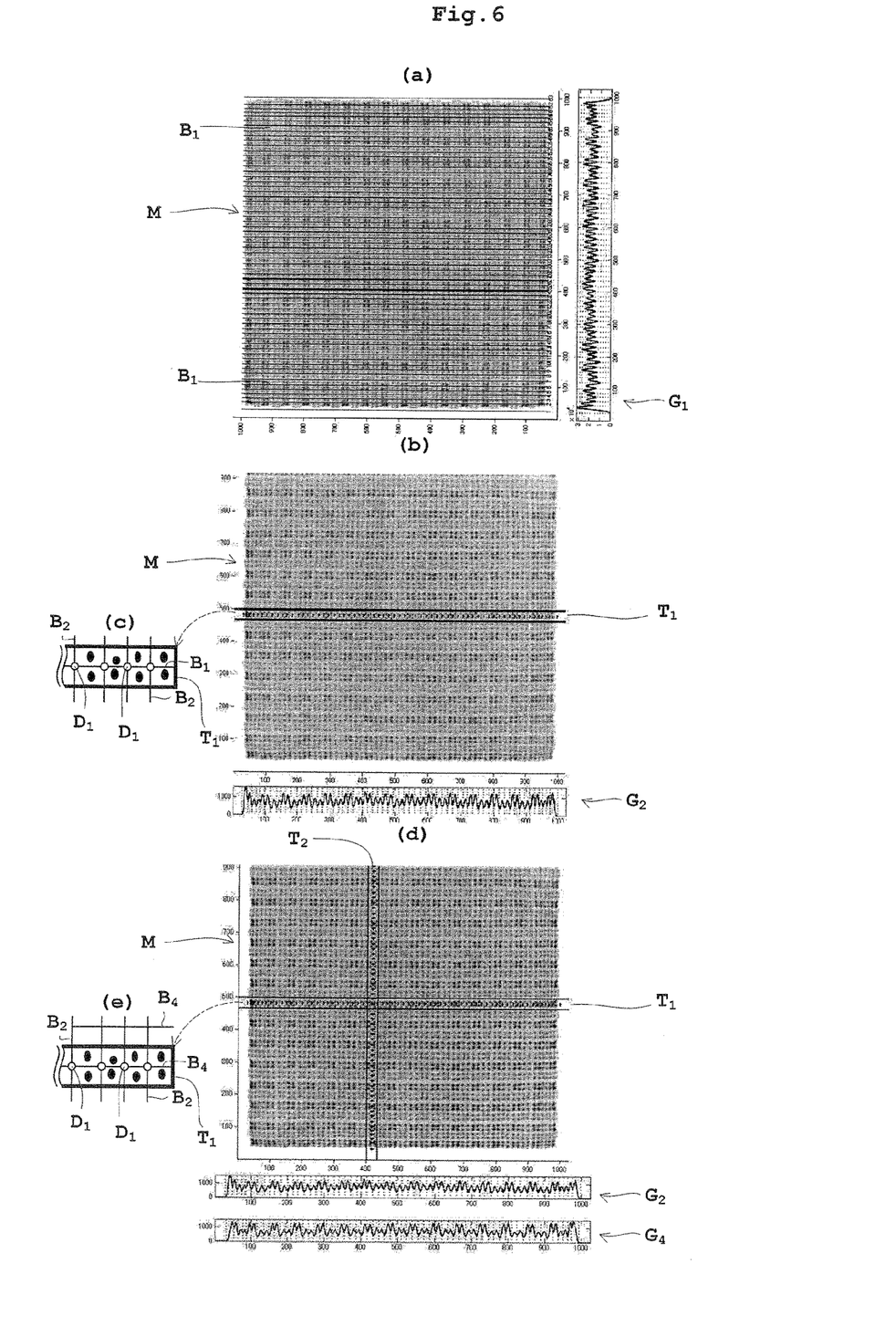
FIG. 6 is a plan view of the two-dimensional position map for use in description of the grid partitioning in FIGS. 4 and 5.
Figure 7:
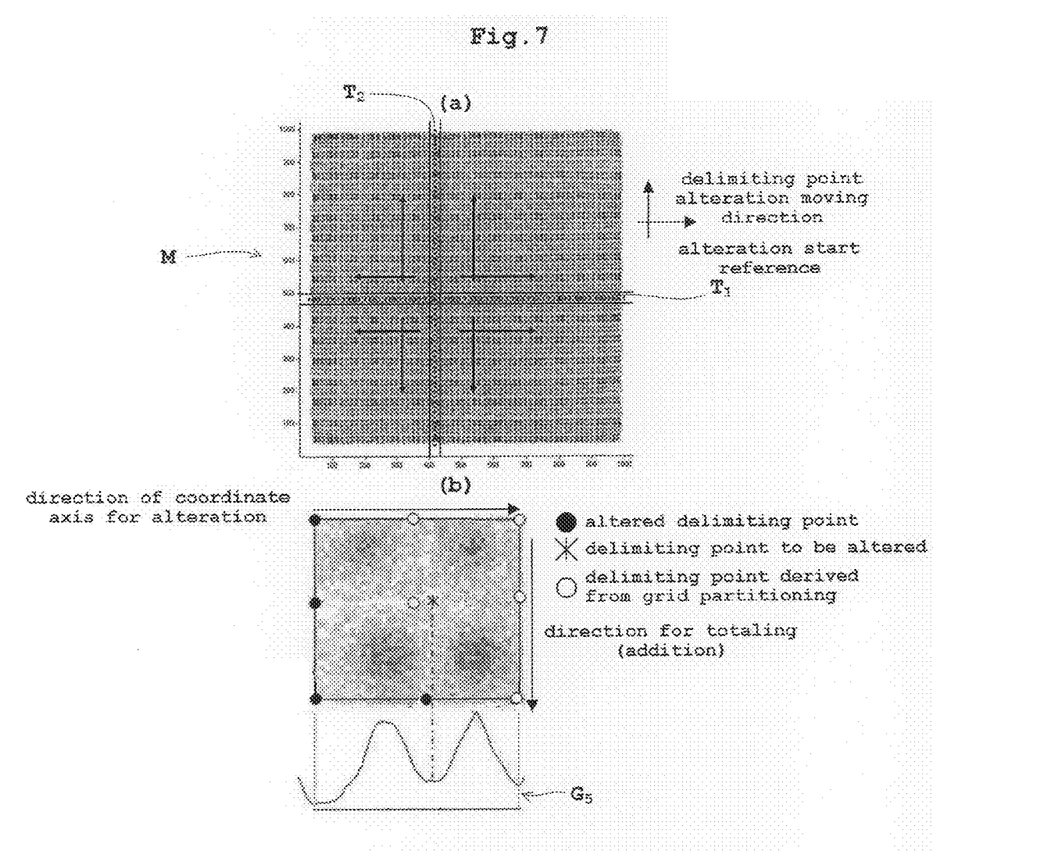
FIG. 7 is a plan view of the two-dimensional position map for use in description of delimiting point alteration in FIG. 4.
Figure 8:
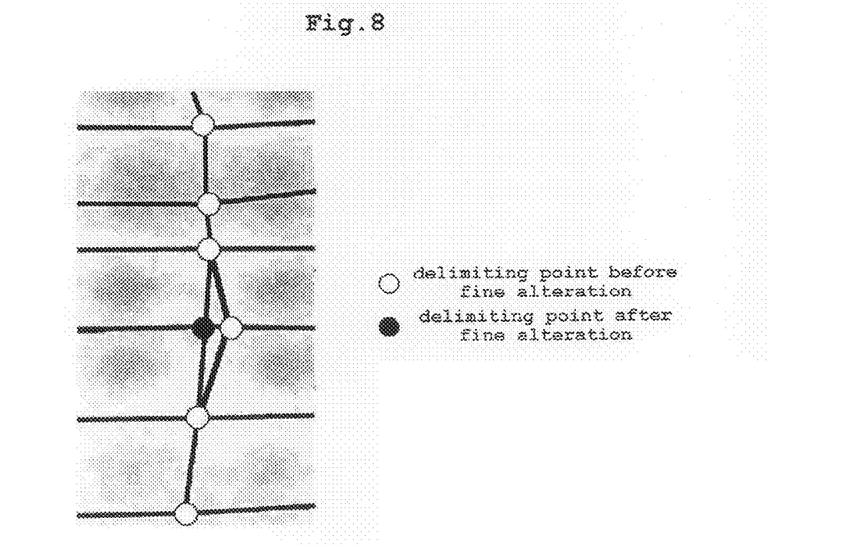
FIG. 8 is a plan view of the two-dimensional position map for use in description of delimiting point fine alteration in FIG. 4.

Next, arithmetic processes by the two-dimensional position map correcting unit 13 will be described with reference to FIGS. 4-8. FIG. 4 is a flow chart showing the arithmetic processes by the two-dimensional position map correcting unit. FIG. 5 is a flow chart showing arithmetic processes of grid partitioning in FIG. 4. FIG. 6 is a plan view of the two-dimensional position map for use in description of the grid partitioning in FIGS. 4 and 5. FIG. 7 is a plan view of the two-dimensional position map for use in description of delimiting point alteration in FIG. 4. FIG. 8 is a plan view of the two-dimensional position map for use in description of delimiting point fine alteration in FIG. 4.

(Step S10) Input two-dimensional position map A two-dimensional position map is inputted (see FIG. 10). Specifically, after an Na-22 radiation source carries out uniform irradiation from above the γ-ray detectors 3 to obtain a two-dimensional position map and before carrying out an actual nuclear medicine diagnosis, a table is prepared by carrying out area division and labeling the entire map with location numbers of the scintillator elements, and is written and stored in the look-up table 10. In this embodiment, the two-dimensional position map is an image of 1024 ×1024 pixels, and the look-up table (LUT) has location numbers of the scintillator elements in the arrangement of 1024 ×1024. That is, on the look-up table (LUT), the respective positions (1024×1024 pixels) in the two-dimensional position map and the respective scintillator elements are in correspondence to one another.

(Step S20) Grid Partitioning

Grid partitioning is carried out after the two-dimensional position map is inputted in step 10.

(Step S21) Determine Count Range

Specifically, in order to determine a count range, count values of one portion of the two-dimensional position map are added. In this embodiment, count values of one portion along both the rows and columns forming the two-dimensional position map are added (which is called "first addition"). That is, totals of count values along the direction of each coordinate axis of the two-dimensional position map are obtained, respectively. As shown in FIG. 6(a), for example, totals of count values along the direction of the coordinate axis relating to the rows of the two-dimensional position map M are obtained, respectively. At this time, for a portion where count values overlap, or when a count value is shared by two areas, because of an insufficient area division, the overlapping count values may both be added, and the count value shared by two areas may be added to one of them. A portion where count values overlap, or a count value being shared by two areas, is the case of distortion, or the case of an end area of the two-dimensional position map M. Preferably, therefore, count values of portions along the rows and columns except for those areas may be added.

As shown in FIG. 6(a), when totals of count values along the direction of the coordinate axis relating to the rows of the two-dimensional position map M have been obtained, respectively, results of addition for the above one portion (in this case, one portion along the rows) are compared to determine respective local minimal values, and respective boundaries are drawn along positions of these local minimal values. In this embodiment, when totals of count values along the direction of the coordinate axis relating to the rows of the two-dimensional position map M have been obtained, respectively, the totals of count values which are results of addition are compared to determine respective local minimal values, and respective boundaries are drawn along positions of these local minimal values and along the rows. Specifically, a graph $G_1$ is prepared, with a horizontal axis representing the direction of the coordinate axis relating to the columns which is perpendicular to the direction of the coordinate axis relating to the rows, and a vertical axis representing the totals (sums) of count values. And points having the local minimal values in the graph $G_1$ are selected. In this embodiment, these points are called "provisional delimiting reference points". At the provisional delimiting reference points, straight parallel lines are drawn along the coordinate axis (in this case, the coordinate axis relating to the rows) on the two-dimensional position map M, to divide the two-dimensional position map M into a plurality of belts. These straight lines are termed boundaries $B_1$ in FIG. 6(a).

And the count values at each boundary $B_1$ are added (which is called "second addition"). In this embodiment, for every two adjacent belts including the belts divided by this boundary $B_1$, a total of the count values of the pixels included in the area of these two belts is obtained. For each belt divided by this boundary $B_1$, a total of the count values of the pixels included in the area of this one belt may be obtained.

When a total of the count values of the pixels included in the area of the two belts has been obtained, one area (in this embodiment, it is called "count range") serving as a reference is set based on the result of addition. In this embodiment, when a total of the count values of the pixels included in the area of the two belts has been obtained, the total of the count values which is the result of addition is compared with totals of the count values in other areas, and areas having the largest and the second largest totals are determined to be the count range. The largest and second largest areas are selected in case the data of the largest itself is in error. Of course, only the largest area may be determined as the count range. End areas and areas with large belt widths and highly influenced by distortion on the two-dimensional position map M are excluded. The count range is termed reference area $T_1$ in FIG. 6(b).

As is clear from the above description, this step S21 corresponds to the first adding step in this invention, the boundary drawing step in this invention, the second adding step in this invention, and the area setting step in this invention.

(Step S22) Determine Delimiting Reference Points

When reference area $T_1$ (count range) has been determined in step S21, the count values in the area $T_1$ (count range) which includes the largest and second largest areas are compared to obtain local minimal values, respectively, and positions of these local minimal values are determined to be delimiting reference points. Specifically, when reference area $T_1$ (count range) has been determined, a graph $G_2$ is prepared, with a horizontal axis representing the area $T_1$ along the rows and a vertical axis representing the totals of count values. And points having the local minimal values in the graph $G_2$ are selected as delimiting reference points. These delimiting reference points are termed delimiting reference points $D_1$ in FIG. 6(c) which is an enlargement a portion of FIG. 6(b). This step S22 corresponds to the delimiting reference point determining step in this invention.

(Step S23) Prepare Delimiting Grid

When delimiting reference points $D_1$ have been determined in step S22, respective boundaries $B_1$ are redrawn along the respective delimiting reference points $D_1$. Specifically, boundaries are redrawn along the columns perpendicular to the boundaries $B_1$ drawn along the rows. By this redrawing, a delimiting grid is formed on the two-dimensional position map M, thereby carrying out grid partitioning consisting of steps S21-S23. These redrawn boundaries are termed boundaries $B_2$ in FIG. 6(c).

Thus, in FIGS. 6(a)-6(c), totals of the count values are obtained, respectively, along the direction of the coordinate axis relating to the rows of the two-dimensional position map M, and the graph $G_1$ is prepared, with the horizontal axis representing the direction of the coordinate axis relating to the columns which is perpendicular to the direction of the coordinate axis relating to the rows, and the vertical axis representing the totals (sums) of count values. The points having the local minimal values (provisional delimiting reference points) in the graph $G_1$ are selected. At these provisional delimiting reference points, parallel boundaries $B_1$ are drawn along the coordinate axis relating to the rows on the two-dimensional position map M. A total of the count values of the respective pixels included in the areas divided by each boundary $B_1$ is obtained to set the area $T_1$ along the rows. The graph $G_2$ is prepared, with the horizontal axis representing the area $T_1$ along the rows and the vertical axis representing the totals of count values. The points having the local minimal values (delimiting reference points $D_1$) in the graph $G_2$ are selected. The boundaries $B_2$ are redrawn along the respective delimiting reference points $D_1$ and along the columns to prepare a delimiting grid along the direction of the columns, thereby carrying out grid partitioning in the direction of the columns. Similarly, the same procedure may be followed to carry out grid partitioning along the direction of the rows.

That is, totals of the count values are obtained, respectively, along the direction of the coordinate axis relating to the columns of the two-dimensional position map M, and a graph $G_3$ (not shown in FIG. 6) is prepared, with a horizontal axis representing the direction of the coordinate axis relating to the rows which is perpendicular to the direction of the coordinate axis relating to the columns, and a vertical axis representing the totals (sums) of count values. The points having the local minimal values (provisional delimiting reference points) in the graph $G_3$ are selected. At these provisional delimiting reference points, parallel boundaries $B_3$ (not shown in FIG. 6) are drawn along the coordinate axis relating to the columns on the two-dimensional position map M. A total of the count values of the respective pixels included in the areas divided by each boundary $B_3$ is obtained to set an area $T_2$ along the columns (see FIG. 6(d)). A graph $G_4$ (see FIG. 6(d)) is prepared, with a horizontal axis representing the area $T_1$ along the columns and a vertical axis representing the totals of count values. The points having the local minimal values (delimiting reference points $D_2$ (not shown in FIG. 6)) in the graph $G_2$ are selected. Boundaries $B_4$ (see FIG. 6(e)) are redrawn along the respective delimiting reference points $D_2$ and along the rows to prepare a delimiting grid along the direction of the rows, thereby carrying out grid partitioning in the direction of the rows.

The grid partitioning along the direction of the columns (steps S21-S23) and the grid partitioning along the direction of the rows (steps S21-S23) may be carried out in parallel. The grid partitioning along the direction of the rows (steps S21-S23) may be carried out after the grid partitioning along the direction of the columns (steps S21-S23). Conversely, the grid partitioning along the direction of the columns (steps S21-S23) may be carried out after the grid partitioning along the direction of the rows (steps S21-S23).

As is clear from the above description, this step S23 corresponds to the boundary redrawing step in this invention.

(Step S30) Delimiting Point Alteration

The positions of delimiting points to be altered are altered by comparing respective count values around the delimiting points to be altered, while successively and contiguously moving from one to another of the boundaries $B_2$ and $B_4$ redrawn in step S23, with reference to the areas $T_1$ and $T_2$ set in step S21. In this embodiment, the area where the areas $T_1$ and $T_2$ cross each other is the alteration start reference. This alteration start reference is the reference point which is the delimiting reference point $D_1$ and also the delimiting reference point $D_2$. From this alteration start reference, alteration is made in the direction of each coordinate axis along the directions of arrows in FIG. 7(a) (delimiting point alteration moving directions). This alteration is carried out for successive adjacent boundaries $B_2$ and $B_4$, in other words, while moving from one to another of adjacent delimiting points, thereby altering all the delimiting points.

As shown in FIG. 7(b), for example, in altering the delimiting points, a partial total graph $G_5$ with a horizontal axis representing the direction of the coordinate axis for alteration and a vertical axis representing the total (sum) of the count values added in a direction normal to the coordinate axis is obtained for an area surrounded by eight delimiting points around a delimiting point to be altered. Each boundary is redrawn based on the partial total graph $G_5$ which is an alteration result. The black dots ("●" in FIG. 7) indicate altered delimiting points, the asterisk ("*" in FIG. 7) indicates the delimiting point to be altered, and the white circles ("○" in FIG. 7) indicate delimiting points derived from the grid partitioning. The position of the delimiting point is altered by regarding the position coordinates of a local minimal value derived from the partial total graph $G_5$ as altered coordinates of the delimiting point. This step S30 corresponds to the altering step in this invention.

(Step S40) Delimiting Point Fine Alteration

The positions of the delimiting points are re-altered by comparing the respective delimiting points belonging to the boundaries redrawn based on the alteration results in step S30. This re-alteration is smaller than the alteration in step S30, and is therefore defined as "fine alteration" in this specification. This embodiment obtains absolute values of differences (hereinafter referred to simply as "difference values") between the coordinates of delimiting points adjacent each other in the direction of the coordinate axis for alteration, and obtains an average value of the difference values of the delimiting points remaining after excluding one delimiting point having the largest increment of coordinates. Next, it is determined for each delimiting point whether a sum of difference values to the adjacent delimiting points corresponds at least to predetermined times (e.g. four times) the average value of the difference values. When the sum of difference values to the adjacent delimiting points corresponds at least to the predetermined times the average value of the difference values, that delimiting point is determined to be an outstanding point with discontinuity. Conversely, when the sum of difference values to the adjacent delimiting points is less than the predetermined times the average value of the difference values, that delimiting point is determined not to stand out but to maintain continuity. And when determined to be discontinuous, the position of the delimiting point is fine-altered by making the average value of the coordinates of the adjacent delimiting points the coordinates after fine alteration.

The white circles ("○" in FIG. 8) indicate delimiting points before the fine alteration, and the black dot ("●" in FIG. 7) a delimiting point after the fine alteration. It will be seen that the first to third upper white circles and the first and second white circles from the bottom in FIG. 8 maintain continuity, and that only the third white circle from the bottom stands out with discontinuity. Then, the delimiting point of the third white circle from the bottom can be re-altered to the position of the delimiting point of the black dot by fine alteration. Based on the delimiting point indicated by the black dot reflecting the re-alteration result, each boundary is redrawn as shown in FIG. 8.

As is clear from the above description, this step S40 corresponds to the re-altering process in this invention.

(Step S50) Prepare Look-Up Table

Through the above steps S10-S40 (including also steps S21-S23), the two-dimensional position map correcting unit 13 reads the two-dimensional position map from the look-up table 10 and, by rewriting and correcting it, prepares a look-up table.

Figure 9:
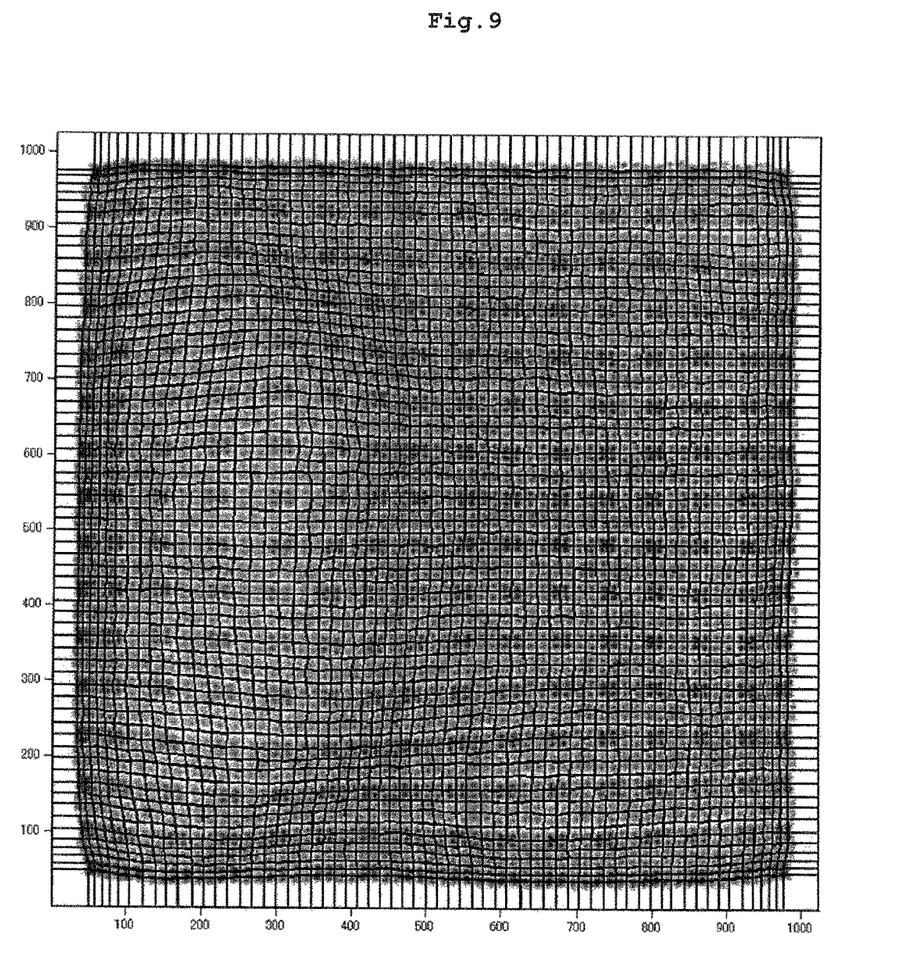
FIG. 9 is a plan view showing an example of area discrimination of the two-dimensional position map which is a correction result.

FIG. 9 shows a plan view showing an example of area discrimination of the two-dimensional position map which is a correction result. FIG. 9 shows a case where the arrangement of scintillator element areas has distortion (there is distortion in areas leftward from the center in FIG. 9). It is confirmed in FIG. 9 also that, even when there is such distortion, discrimination can be made by correcting the two-dimensional position map. Further, it is confirmed in FIG. 9 also that, by redrawing boundaries to make alteration and fine alteration (re-alteration), the boundaries are redrawn in the areas with distortion, and grid partitioning is carried out as divided by the redrawn boundaries.

With the radiation detecting apparatus (gantry 2, γ-ray detector 3, position calculating circuit 9, look-up table 10, coincidence circuit 11 and two-dimensional position map correcting unit 13) provided for the PET apparatus according to this embodiment having above construction, the two-dimensional position map correcting unit 13 executes step S21 (determination of count range) for adding count values as signal strengths of one portion (one portion along both the rows and columns in this embodiment) of the two-dimensional position map, draws each of the boundaries $B_1$ and $B_3$ based on the result of addition (total of count values in one portion along the rows and columns in this embodiment) in step S21, and corrects the two-dimensional position map based on the count values enclosed by these boundaries $B_1$ and $B_3$. Since count values of one portion of the two-dimensional position map, and not all the areas of the two-dimensional position map, are added, the two-dimensional position map can be corrected efficiently.

In this embodiment, count values of each portion (portion along both the rows and columns in this embodiment) of the two-dimensional position map are added, respectively. The respective results of addition for each portion (totals of the count values for the portion along both the rows and columns in this embodiment) are compared (local minimal values are selected in this embodiment), and the boundaries $B_1$ and $B_3$ are drawn, respectively. The count values at the respective boundaries $B_1$ and $B_3$ are added, and reference areas $T_1$ and $T_2$ (count ranges in this embodiment) are set, one for each of the row and column, based the results of addition (total of the count values of the pixels included in the areas of two adjacent belts including the belts divided by the boundaries $B_1$ and $B_3$ in this embodiment). And in step S22 (determination of delimiting reference points), respective delimiting reference points $D_1$ and $D_2$ are determined based on the respective count values in the reference areas $T_1$ and $T_2$ (count ranges in this embodiment) set in step S21. Further, the respective boundaries $B_1$ and $B_3$ are redrawn along the respective delimiting reference points $D_1$ and $D_2$ determined in step S22, to serve as redrawn boundaries $B_2$ and $B_4$.

Regarding the boundaries $B_1$ and $B_1$ drawn previously, the respective boundaries $B_1$ and $B_3$ drawn by comparing (selecting local minimal values in this embodiment) the respective results of addition for each portion (totals of the count values for one portion along both the rows and columns in this embodiment), but they are not boundaries taking distortion into consideration, and the areas enclosed by the boundaries $B_1$ and $B_3$ are not exact, either. Then, the count values at the respective boundaries $B_1$ and $B_3$ are added, and reference areas $T_1$ and $T_2$ (count ranges in this embodiment) are set, one for each of the row and column, based the results of addition (total of the count values of the pixels included in the areas of two adjacent belts including the belts divided by the boundaries $B_1$ and $B_3$ in this embodiment). And in step S22, respective delimiting reference points $D_1$ and $D_2$ are determined based on the respective count values in the reference areas $T_1$ and $T_2$ (count ranges in this embodiment) set in step S21. In the subsequent step S23 (preparation of partitioning grid), the respective boundaries $B_1$ and $B_3$ are redrawn along the respective delimiting reference points $D_1$ and $D_2$ determined in step S22, to serve as redrawn boundaries $B_2$ and $B_4$.

In this embodiment, preferably, step S30 (correction of delimiting points) is executed. That is, the positions of delimiting points to be altered are altered by comparing is respective count values around the delimiting points to be altered, while successively and contiguously moving from one to another of the boundaries $B_2$ and $B_4$ redrawn in step S23, with reference to the areas $T_1$ and $T_2$ (count ranges in this embodiment) set in step S21. Each boundary is redrawn based on the partial total graph $G_5$ which is an alteration result, and the two-dimensional position map is corrected based on the count values enclosed by these boundaries. Consequently, the boundaries have distortion taken into consideration, and the two-dimensional position map can be corrected accurately even when there is distortion.

The farther away from the areas $T_1$ and. $T_2$ (count ranges in this embodiment) set in step S21, the larger becomes distortion (see FIG. 9). Therefore, in step S30, the positions of delimiting points to be altered are altered by comparing respective count values around the delimiting points to be altered, while successively and contiguously moving from one to another of the boundaries $B_2$ and $B_4$ redrawn in step S23. Thus, the positions of delimiting points are altered while successively and contiguously moving from one to another of the boundaries $B_2$ and $B_1$ redrawn in step S23, with reference to the areas $T_1$ and $T_2$ (count ranges in this embodiment) set in step S21. The positions of delimiting points can be altered accurately using respective surrounding count values already altered. Therefore, each boundary is redrawn based on the partial total graph $G_5$ which is an alteration result in the altering step, and the areas enclosed by these boundaries have increased accuracy, allowing the two-dimensional position map to be corrected with increased accuracy.

When altering the positions of delimiting points as in step S30, preferably, re-alteration is carried out as in step S40 (delimiting point fine alteration) described above. The positions of delimiting points are re-altered by comparing the respective delimiting points belonging to the boundaries redrawn based on the alteration results in step S30. Each boundary is redrawn based on the delimiting points indicated by the black dot ("●" in FIG. 8) which are the re-alteration result, and the two-dimensional position map is corrected based on the count values enclosed by these boundaries.

In step S40, the positions of delimiting points are re-altered by comparing the respective delimiting points belonging to the boundaries redrawn based on the alteration results in step S30. That is, discontinuity will remain even if each boundary is redrawn based on the alteration results in step S30 which are the previous alterations. Then, whether discontinuity or continuity is determined by comparing the respective delimiting points belonging to the boundaries redrawn based on the alteration results in step S30, and in the discontinuous case, the positions of delimiting points are re-altered. Since the positions of delimiting points are re-altered in this way by comparing the respective delimiting points belonging to the boundaries redrawn based on the alteration results in step S30, discontinuity can be eliminated and the delimiting points can be re-altered with increased accuracy. Therefore, each boundary is redrawn based on the results of re-alteration in step S40, and the areas enclosed by these boundaries will also become further accurate to allow the two-dimensional position map to be corrected with increased accuracy.

When drawing the previous boundaries $B_1$ and $B_3$, preferably, each local minimal value is obtained by comparing the results of addition for each portion in the first addition (totals of the count values in one portion along the rows and columns in this embodiment), and the boundaries $B_1$ and $B_3$ are drawn along the positions of these local minimal values, respectively. The respective boundaries $B_1$ and $B_3$ can be drawn accurately by obtaining the local minimal values.

Similarly, in step S22, preferably, each local minimal value is obtained by comparing the respective count values in the reference areas $T_1$ and $T_2$ (count ranges in this embodiment) set in step S21, and the positions of these local minimal values are determined to be delimiting reference points $D_1$ and $D_2$. The delimiting reference points $D_1$ and $D_2$ can be determined accurately by obtaining the local minimal values.

In this embodiment, in the first addition, count values in one portion along at least one (both in this embodiment) of the rows and columns constituting the two-dimensional position map are added, and each boundary $B_1$, $B_3$ is drawn along at least one (both in this embodiment) of the rows and columns based on the result of addition (totals of count values in one portion along the rows and columns in this embodiment). The two-dimensional position map is corrected based on the count values enclosed by these boundaries $B_1$ and $B_3$.

This invention is not limited to the foregoing embodiment, but may be modified as follows:

(1) In the foregoing embodiment, a PET apparatus has been described as an example of nuclear medicine diagnostic apparatus having the radiation detecting apparatus. This invention is applicable also to a SPECT (Single Photon Emission CT) apparatus which detects a single γ-ray to reconstruct a sectional image of a patient. It is applicable also to a PET-CT apparatus which is a combination of a PET apparatus and a CT apparatus. It is applicable also to radiation other than γ (e.g. α-rays, β-rays and so on).

(2) The foregoing embodiment provides DOI detectors each having of a plurality of scintillator elements arranged in three dimensions. The invention is applicable also to radiation detectors each having a plurality of scintillator elements arranged in two dimensions or three dimensions.

(3) In the foregoing embodiment, the photomultiplier tubes (PMT) have been described as an example of light sensors. There is no limitation as long as light sensors are optically coupled to the scintillator elements, as exemplified by avalanche photodiodes and silicon photomultipliers.

(4) The foregoing embodiment has employed count values as signal strengths. However, electric signals having continuous values may be employed as signal strengths.

(5) In the foregoing embodiment, local minimal values are obtained to draw each boundary along positions of the local minimal values, and to determine them to be delimiting reference points. Local maximal values may be employed instead. However, when count values are employed as signal strengths as in the foregoing embodiment, it is more desirable to employ local minimal values as in the embodiment since the boundaries of the two-dimensional position map correspond to portions of the local minimal values.

(6) In the foregoing embodiment, signal strengths (count values in the embodiment) in one portion along the rows and columns forming the two-dimensional position map are added, respective boundaries are drawn along both the rows and columns based on the results of addition, and the two-dimensional position map is corrected based on the signal strengths (count values) enclosed by these boundaries. However, it is not limited to both the rows and columns. Application may be made to only the rows, or application may be made to only the columns, as long as signal strengths (count values) in one portion along at least either the rows or columns are added, respective boundaries are drawn along at least either the rows or columns based on the results of addition, and the two-dimensional position map is corrected based on the signal strengths (count values) enclosed by these boundaries. Application may be made to only the rows, or application may be made to only the columns, also when altering and re-altering (fine-altering) the delimiting points.

The invention claimed is:

1. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising a first adding step for adding the signal strengths in a portion of the two-dimensional position map, wherein respective boundaries are drawn based on results of addition in the first adding step, and the two-dimensional position map is corrected based on signal strengths enclosed by these boundaries and wherein the first adding step is executed to add the signal strengths of each portion of the two-dimensional position map; the method comprising a boundary drawing step for drawing the respective boundaries by comparing results of addition of the each portion in the first adding step; a second adding step for adding the signal strengths at the respective boundaries; an area setting step for setting one reference area based on results of addition in the second adding step; a delimiting reference point, determining step for determining respective delimiting reference points based on respective signal strengths in the reference area set in the area setting step; and a boundary redrawing step for redrawing respective boundaries along the respective delimiting reference points determined in the delimiting reference point determining step; the two-dimensional position map being corrected based on signal strengths enclosed by the boundaries redrawn in the boundary redrawing step.

2. The two-dimensional position map correcting method according to claim 1, comprising an altering step for altering positions of delimiting points to be altered, by comparing respective signal strengths around the delimiting points to be altered, while successively and contiguously moving from one to another of the boundaries redrawn in the boundary redrawing step, with reference to the area set in the area setting step, wherein the respective boundaries are redrawn based on results of addition in the altering step, and the two-dimensional position map is corrected based on signal strengths enclosed by these boundaries.

3. The two-dimensional position map correcting method according to claim 2, comprising an re-altering step for re-altering the positions of the delimiting points by comparing respective delimiting points belonging to the boundaries redrawn based on results of alteration in the altering step, wherein the respective boundaries are redrawn based on results of re-alteration in the re-altering step, and the two-dimensional position map is corrected based on signal strengths enclosed by these boundaries.

4. The two-dimensional position map correcting method according to claim 1, wherein the boundary drawing step is executed to obtain respective local minimal values by comparing the results of addition of the each portion in the first adding step, and to draw the respective boundaries along positions of these local minimal values.

5. The two-dimensional position map correcting method according to claim 1, wherein the delimiting reference point determining step is executed to obtain respective local minimal values by comparing the signal strengths in the reference area set in the area setting step, and to determine positions of these local minimal values to be the delimiting reference points.

* * * * *